(12) United States Patent
Weig

(10) Patent No.: US 10,045,877 B2
(45) Date of Patent: Aug. 14, 2018

(54) OSTOMY APPLIANCES FOR EFFLUENT CONTROL

(75) Inventor: Bret Weig, Browns Mills, NJ (US)

(73) Assignee: CONVATEC TECHNOLOGIES INC., Las Vegas, NV (US)

( * ) Notice: Subject to any disclaimer, the term of this patent is extended or adjusted under 35 U.S.C. 154(b) by 52 days.

(21) Appl. No.: 12/999,646

(22) PCT Filed: Jun. 19, 2009

(86) PCT No.: PCT/US2009/047992
§ 371 (c)(1),
(2), (4) Date: Dec. 17, 2010

(87) PCT Pub. No.: WO2009/155537
PCT Pub. Date: Dec. 23, 2009

(65) Prior Publication Data
US 2011/0092929 A1 Apr. 21, 2011

Related U.S. Application Data

(60) Provisional application No. 61/073,986, filed on Jun. 19, 2008.

(51) Int. Cl.
*A61F 5/445* (2006.01)

(52) U.S. Cl.
CPC ...... *A61F 5/445* (2013.01); *A61F 2005/4455* (2013.01)

(58) Field of Classification Search
CPC ... A61B 1/32; A61B 17/0293; A61B 17/3423; A61B 17/3431; A61B 17/3484;
(Continued)

(56) References Cited

U.S. PATENT DOCUMENTS 3,509,884 A * 5/1970 Bell ............... A61M 25/04
604/101.05
3,675,658 A * 7/1972 Taylor ............ A61M 25/10185
251/143

(Continued)

FOREIGN PATENT DOCUMENTS

EP 0168967 1/1986
EP 1346711 3/2002
(Continued)

OTHER PUBLICATIONS

"Stoma". Webster's New World Medical Dictionary. 2008. http://search.credoreference.com/contentientry/webstermed/stoma/0 (May 30, 2015).*

(Continued)

*Primary Examiner* — Susan Su
(74) *Attorney, Agent, or Firm* — Wilson Sonsini Goodrich & Rosati

(57) ABSTRACT

A stoma extender includes a first end for insertion into a stoma for diverting stomal effluent into the stoma extender before the effluent exits the stoma; a second end for remaining external of the stoma, for providing a discharge exit for stomal effluent; and a conduit portion coupled between the first and second ends for communicating stomal effluent through the stoma extender, wherein the length of the conduit portion is adjustable stably, to permit adaptation of the stoma extender to an individual's stoma.

21 Claims, 11 Drawing Sheets

(58) Field of Classification Search
CPC .... A61F 2/02; A61F 5/445; A61F 2005/4455; A61F 2005/4483; A61F 5/448; A61F 5/449; A61F 2005/4486; A61F 2005/4495
USPC .......................... 604/332–345; 600/580–582
See application file for complete search history.

(56) References Cited

U.S. PATENT DOCUMENTS

| | | | | |
|---|---|---|---|---|
| 3,938,521 | A * | 2/1976 | Ritota | A61F 5/455 604/328 |
| 4,137,918 | A * | 2/1979 | Bogert | A61F 5/445 604/275 |
| 4,231,369 | A * | 11/1980 | Sorensen et al. | 604/336 |
| 4,601,713 | A * | 7/1986 | Fuqua | A61M 25/0023 604/103.14 |
| 4,662,890 | A * | 5/1987 | Burton | A61F 5/445 128/899 |
| 4,721,508 | A * | 1/1988 | Burton | A61F 5/445 604/103.03 |
| 4,950,223 | A | 8/1990 | Silvanov | |
| 5,125,916 | A | 6/1992 | Panebianco et al. | |
| 5,366,478 | A * | 11/1994 | Brinkerhoff | A61B 17/3423 248/56 |
| 5,520,669 | A * | 5/1996 | Mulholland | A61F 5/451 604/328 |
| 5,524,644 | A | 6/1996 | Crook | |
| 5,634,937 | A * | 6/1997 | Mollenauer | A61B 17/00234 604/115 |
| 5,941,860 | A * | 8/1999 | Wheeler | A61F 5/451 604/327 |
| 6,033,390 | A | 3/2000 | Von Dyck | |
| 6,846,287 | B2 * | 1/2005 | Bonadio et al. | 600/208 |
| 6,958,037 | B2 * | 10/2005 | Ewers et al. | 600/208 |
| 7,001,367 | B2 * | 2/2006 | Arkinstall | A61F 5/445 604/337 |
| 7,258,661 | B2 * | 8/2007 | Davies et al. | 600/32 |
| 7,347,844 | B2 * | 3/2008 | Cline | A61F 5/448 604/336 |
| 7,559,893 | B2 * | 7/2009 | Bonadio | A61B 17/0293 600/208 |
| 7,765,006 | B2 * | 7/2010 | Martino et al. | 607/40 |
| 8,343,028 | B2 * | 1/2013 | Gregoric | A61B 17/11 600/16 |
| 8,939,952 | B2 * | 1/2015 | Weig | A61F 2/0027 604/101.05 |
| 2003/0040768 | A1 * | 2/2003 | Greene | A61B 17/0057 606/190 |
| 2003/0220621 | A1 | 11/2003 | Arkinstall | |
| 2004/0168950 | A1 | 9/2004 | Barker | |
| 2004/0193122 | A1 * | 9/2004 | Cline | A61F 5/448 604/332 |
| 2005/0033226 | A1 | 2/2005 | Kim | |
| 2005/0090717 | A1 | 4/2005 | Bonadio | |
| 2006/0058576 | A1 * | 3/2006 | Davies et al. | 600/32 |
| 2007/0213661 | A1 * | 9/2007 | Gobel | A61F 2/0013 604/96.01 |
| 2007/0282161 | A1 | 12/2007 | Ferguson | |
| 2008/0119803 | A1 | 5/2008 | Cline | |

FOREIGN PATENT DOCUMENTS

| WO | WO-2008103789 A2 | 8/2008 |
|---|---|---|
| WO | WO-2008157172 A1 | 12/2008 |

OTHER PUBLICATIONS

"Stoma". The American Heritage Medical Dictionary. 2007. http://search.credoreference.com/content/entry/hmmedicaldict/stoma/0 (May 30, 2015).*

Australia Patent Application No. 2015246069 Patent Examination Report No. 1 dated Sep. 8, 2016.

European Patent Application No. 17170196.4 extended European Search Report dated Jan. 22, 2018.

Canadian Patent Application No. 2,967,491 Office Action dated May 3, 2018.

* cited by examiner

OSTOMY APPLIANCES FOR EFFLUENT CONTROL

CROSS-REFERENCE

This application is filed pursuant to 35 U.S.C. § 371 as a United States National Phase Application of International Application Ser. No. PCT/US09/47992, filed Jun. 19, 2009, which claims the benefit of and the right of priority to U.S. Patent Application No. 61/073,986 filed Jun. 19, 2008, both of which are incorporated by reference herein in their entirety.

The present invention relates to the field of ostomy appliances for fitting and sealing within and around an ostomate's stoma to direct effluent output. Other aspects of the invention relate to the ability to adjust to the varying distance between the fascia and the skin and the ability to "self-inflate" via fluidic actuation. The term "ostomy" is intended to cover at least colostomy, ileostomy and urostomy.

BACKGROUND TO THE INVENTION

Effectively directing or otherwise controlling effluent output is central to ostomy devices designed to protect skin adjacent to the discharge area. Creating a seal around a person's stoma, such that the seal is dependable, comfortable and conducive to body tissue, is important for the function of ostomy appliances. Once this seal has been made, the appliance may use one or more of a variety of techniques for managing stomal discharge. The formation of such a seal remains an area of continuous improvement and development, since the performance and comfort of the seal is fundamental to customer acceptance. The protection of the external peristomal tissue where the normal skin and stoma tissue meet is an essential characteristic of such an ostomy device. Peristomal tissue can be extremely sensitive. Irritation can result if the peristomal tissue is exposed to body waste, or to repeated application and removal of adhesive or other sealants.

Ideally, the stoma should protrude from the abdominal surface of the ostomate by a distance ranging from 0.5 cm to 2.5 cm. This protrusion forms a spout, from which effluent can discharge directly into the pouch. However, in many cases, the stoma protrudes by a lesser amount or not at all. For example, a "flush stoma" is a condition when the stoma reaches only as far as the surface of the abdomen; a "recessed stoma" is a condition when the stoma does not even reach the surface of the abdomen, and the peristomal skin is drawn into a funnel shaped mouth between the stoma and the abdominal surface. There are many potential causes for these conditions. These can include improper formation of the stoma by the surgeon; and post-operative weight gain by the ostomate. Post-operative weight gain causes the ostomate's abdominal region to expand in girth while the length of the intestine attached to the abdomen remains fixed, thereby resulting in the stoma being pulled toward and ultimately below the surface of the abdomen.

Flush and recessed stomas can be difficult to manage, because some effluent discharged from the stoma can tend to pool around the stoma, instead of the effluent discharging completely into the pouch. Stool retained in this manner can attack the interface between the adhesive body fitment and the ostomate's peristomal skin. Such attack reduces the adhesion of the body fitment to the skin, thereby reducing the effectiveness and the usable life of the appliance. The stool can also cause irritation and degradation of the peristomal skin itself. Stool exiting the stoma may contain digestive juices from the body, and such juices can attack the peristomal skin resulting in excoriation. It is hitherto not known for a single device to accommodate varying distances between the stoma and skin level.

Some known devices use a single expandable balloon or member inside the stoma to form a seal against the inside wall of the opening, and a fixed stop or surface against the outside of the body. However, such devices have to be designed carefully to avoid the risk of damage to the sensitive internal tissue. In such designs, a relatively high concentration of force may be placed on the tissue underneath the stoma, effecting blood circulation in the area under pressure, thereby over time leading to tissue necrosis.

By way of example, U.S. Publication No. 2003/0220621 describes a valved ostomy device including a hollow discharge tube and anchoring means for anchoring the tube in the stoma. The anchoring means comprises an inflatable balloon cuff inserted in the stoma to anchor the tube against the stomal wall, and a screw threaded clamp as an outer stop surface. Although the screw threaded clamp has a conformable pad, the anchoring means bears the entire weight of the ostomy appliance and any collection device attached to it. Thus, the strength of the attachment has to be offset against limitations on the clamping force which can be applied through the peristomal tissue without causing discomfort and tissue damage, and the inflation pressure of the balloon cuff without causing internal tissue damage to the stoma lumen. Additionally, the device has very little or no range of adjustment to the varying distance between the underside of the fascia and the skin, limiting the use to individuals whose fascia-skin distance is within the range of the device. Also, the means of inflating the device requires a secondary mechanism such as a syringe or pump to inflate it. To have the user carry around an extra component is inconvenient, and the inflation mechanism may not have a means to control the amount of fluid to be pumped into the device, which brings associated risks of under or over-inflation of the device.

EP 0168967, EP 1346711 and U.S. Pat. No. 4,950,223 describe ostomy ports comprising a single inflatable balloon inserted into the stoma, and an external adhesive wafer for securing the appliance to the skin around the stoma. Such designs are concerned primarily with the formation of a seal inside the stoma lumen. The peristomal tissue is either unprotected or is protected by the adhesive wafer, leaving the possibility that the peristomal tissue may be vulnerable to the conventional problem of irritation and pain resulting from exposure to stool or repeated applications and removals of adhesive. As in the previous referenced device, there are also no significant accommodations for the variation in fascia-skin distance or the fact that a secondary component is required for inflation.

SUMMARY OF THE INVENTION

The present invention is generally directed to a stoma extender having a first end for insertion into a stoma for diverting stomal effluent into the stoma extender before the effluent exits the stoma, a second end for remaining external of the stoma, for providing a discharge exit for stomal effluent, and a tubular portion or conduit portion coupled between the first and second ends for communicating stomal effluent through the stoma extender.

Optional aspects of the invention include (i) the length of the conduit portion being adjustable stably to enable the stoma extender to be adapted to an individual's stoma; (ii)

a seal for the first end, the seal including a plurality of resilient fingers and elastic webbing extending at least between portions of the fingers; (iii) a seal for the first end, the seal comprising a material configured to expand when contacted by moisture; (iv) a collapsed configuration of the first end and, optionally, a portion of the tubular member or conduit portion, the collapsed configuration being retained by a water-soluble and/or water-dispersible glue or coating, such as gelatin; (v) an inflation fluid reservoir integrated in the stoma extender for inflating a seal at the first end, thereby avoiding the user having to carry additional inflation equipment; and/or (vi) a collar slidable on the tubular member and retained selectively by a selective engagement device. The selective engagement device may be manually operable, or it may be directionally responsive.

These ideas may be used independently, or any two or more of the above ideas may be used in combination. The invention explicitly envisages all such possible combinations and permutations.

There are several embodiments of the invention. These illustrate the above and other aspects of: a means of sealing against the intestinal wall; an ability to adjust to the varying fascia-skin distances and provide an elastic range to accommodate movement; a means of insertion and removal from the stoma; and a feature of "self-inflation" by means of internally containing the fluidic pressure to actuate and/or deploy the device. Each embodiment may incorporate one or more of these aspects.

Additional features usable in combination with this invention are described in applications U.S. Application Nos. 60/891,120 and 60/891,127, the contents of which are hereby incorporated by reference.

Other aspects of the present invention, and additional features usable in combination with the foregoing, include:

(a) The seal may comprise an inflatable chamber portion for sealing against the internal wall of the stoma. The inflatable chamber is toroidal in shape and is sealed to or continuous with a tubular straight, tapered or "trumpet-shape" central channel constructed of a thin elastic material.

(b) The seal may comprise a first inflatable chamber portion for sealing against the internal wall of the stoma, and a second inflatable chamber portion for sealing externally of the stoma.

(c) The seal may be positioned in the aperture of an adhesive member. The seal may include an inflatable chamber portion and a support. The support may provide a backbone for the inflatable chamber portion. The inflatable chamber portion may allow the support to float somewhat with respect to the adhesive member.

(d) The seal may include an inflatable chamber portion that is located in the aperture of an adhesive member, and is configured to seal externally of the stoma, without substantially occluding the stoma. A tubular member or passage may optionally extend through the external inflatable chamber portion for discharge of body waste. The inflatable seal may allow the discharge of body waste without removal of the inflatable seal from the stoma.

(e) The seal comprising the internal portion for sealing against the internal wall of the stoma may be constructed of a non-inflatable toroidal member, i.e., an O-ring. This member is attached and/or bonded to or is of a continuously formed shape with a generally tubular elastic member that extends through the stoma opening creating a passageway out of the body.

(f) The seal comprising the internal portion for sealing against the internal wall of the stoma may be constructed, in the deployed state, of a non-inflatable funnel-shaped member possessing finger-like protrusions, roughly like the supporting members of an umbrella, but in the opposite direction of deployment. These protrusions are continuous with a ringed feature at their base that provides a support to maintain a central opening, in particular, if there is a radial force to effect closing of the fingers. This funnel-shaped member is constructed of flexible and/or elastic material such that it is rigid enough to maintain shape but flexible and soft enough to easily close the fingers to affect a somewhat cylindrical shape. The end of the fingers curve inward with a radius so as to prevent the concentration of force at the finger ends when contacting the intestinal wall. Over this funnel-shaped member is attached/bonded or otherwise constructed continually a thin highly elastic covering, so as to create webbing between the fingers and a sealed central tubular passageway from the end of the supporting ringed feature. The central tubular passageway extends through the stoma opening and out of the body. The central tubular passageway may be of a tubular straight, tapered or "trumpet" shape. Another embodiment may have the supporting ringed feature extend through the stoma and out of the body. A tubular shaped insertion tool may be used to engage the curved ends of the fingers in the closed state. Once the distal end of the device in place inside the stoma the tool is removed and the shape memory of the funnel-shaped member deploys the device. It may be that the highly elastic covering is an over-molding where the fingers, formed originally in a pre-loaded state, are held in tension during the over-molding process so that when the completed device is deployed the highly elastic covering retains a stretched condition to maintain the seal to the intestinal wall.

(g) The seal comprising the internally inflated chamber portion may be constructed of a single chamber or dual interconnecting chambers attached and/or bonded to, or constructed of one formed shape, with a tubular, more firm or rigid central member. The proximal end of this assembly or component may be attached to another more elastic tubular member, or the central member itself continues outside the body, so as to provide a passageway through the device. With embodiments having the other more elastic tubular member, the shape may be tubular straight, tapered or "trumpet-like". The assembly/component comprising the single or dual chambers, and the more firm central tubular member, are to be inserted fully behind the fascia and inflated, while the proximal end of the central member or the more elastic straight, tapered or "trumpet" shaped tubular member remains external to the stoma. This assembly configuration may allow for easy insertion into the stoma opening without the need for an insertion device.

(h) The member comprising the seal external to the stoma may be constructed of a thicker toroidal-shaped elastic material or O-ring such that when the internal member is deployed within the stoma the external member may be manually "rolled up" by the user, utilizing the circumferential detent of the toroidal shape and the elastic rebound of the interconnecting tubular member or passage, so as to accommodate the varying fascia-skin distance. The interconnecting tubular member may comprise the range of characteristics from thin and highly elastic to being constructed of more rigid material, and may be of a tubular tapered or "trumpet" shape.

(i) The member comprising the seal external to the stoma may not only be constructed of a thicker toroidal-shaped elastic material or O-ring for a manual circumferential detent adjustment to the fascia-skin distance, but may also contain a pressurized chamber, i.e., an inflatable O-ring. This chamber is to be pressurized with fluid at manufacture or at some time previous to use, such that the pressure contained, when released, can be utilized to transfer, via elastic action, the fluidic component through interconnecting passageways into the internal chamber so the internal chamber may be deployed while within the body, thereby eliminating the need of a secondary component for inflating the device. An orifice or other fluid restriction, or valve may be used at the entrance, exit or along the interconnecting passageways to delay device deployment to allow the user sufficient time for device insertion. The internal chamber may be constrained, e.g., folded, rolled and/or twisted, into a thin, long shape to ease insertion into the stoma prior to device deployment without the need for an insertion tool. Gelatine or other coating on the constrained internal chamber may facilitate insertion by maintaining the constraint until the gelatine contacts or is within the moist interior of the stoma. The addition of a cap over the internal chamber may also aid in maintaining the chamber in a constrained condition before use.

(j) The member external to the stoma may not comprise an external seal but may only rest or attach and have "vents" allowing fluid escape in the event the internal seal to the intestine is compromised. The effluent venting may prevent occlusion of the stoma opening in the event of seal failure. The effluent venting may also be an indicator that the device is in need of replacement.

(k) The member external to the stoma, with embodiments that have a more firm central tubular member, may be comprised of a more rigid material, effectively a collar, and may possesses features along the contacting surface with the central member such that the collar may be manually placed over and easily slid down the central member but will meet more resistance moving up the central member. This may be accomplished via angled, bendable protrusions with sharp ends extending radially inward and contacting the central member so that movement in one direction (downward or distally) is facilitated but opposite movement (upward or proximally) is restrained. The restrained movement in the proximal direction of the collar may not be full but measured so as to prevent tissue damage in the event of excessive or unexpected body movement. Another embodiment may involve a locking feature within the collar whereas once the collar is in place over the central tubular member a second component of the collar interacts to squeeze the central tubular member sufficiently so as to hold the collar in its position on the member.

(l) Successfully packaging the device embodiments possessing the pressurized external chamber or inflatable O-ring (ref. 'i' above) may be accomplished by utilizing a container pressurized with the same fluid and to the same pressure as the device in the non-deployed state. This may alleviate the problem of the device depressurizing over time due to the permeability of the device materials. The package container may be constructed of barrier films or may be a hard polymer or an aluminum (e.g., like a soda can) or other container that will hold the fluidic pressure over time until the contained device is needed.

(m) The seal comprising the internal portion for sealing against the internal wall of the stoma may be constructed of a rigid tubular member with a semi-spherical bulge at the distal end. The proximal end of the tubular member comprises a generally flange-shaped feature exterior to the body so as to be clear of the stoma and attach to an external wafer or component. Through the bulge are a series of holes. Over the exterior of the tubular member is placed a covering of expandable foam material, which may be generally thicker over the bulge at the distal end. This foam material expands significantly in the presence of moisture. When the device is inserted the moisture and liquid effluent in the stoma pass through the holes in the bulge and over the surface of the foam causing the foam to expand and create a seal against the intestinal wall.

As used herein, the term "inflatable" means a chamber portion that is configured to be expanded by inflating the chamber with a positive inflation pressure (e.g., a pressure of inflation fluid greater than the external pressure).

Features and advantages of the invention may include: providing an ostomy seal that is comfortable and effective without creating high concentrations of pressure internally or externally, and which can produce a comfortable peristomal seal; the ability to adjust to the varying fascia-skin distances and provide an elastic range to accommodate movement; the means of insertion and removal from the stoma; and the feature of "self-inflation" by means of internally containing the fluidic pressure to actuate and/or deploy the device.

Although certain features have been highlighted above and in the appended claims, the Applicant may seek claim protection for any inventive feature and/or idea described and/or illustrated herein whether or not emphasis has been placed thereon.

DETAILED DESCRIPTION OF PREFERRED EMBODIMENTS

Figure 1:
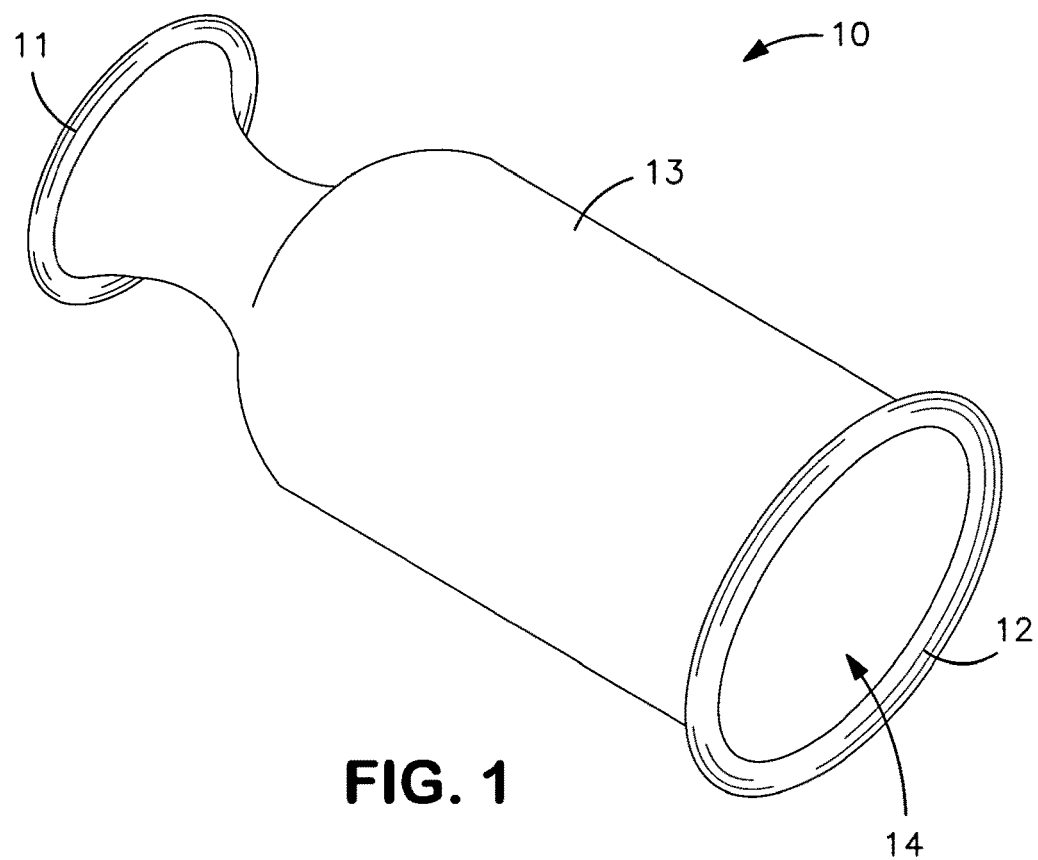
FIG. 1 is a schematic perspective view of a first embodiment of the invention in an "unrolled" condition possessing features described in "e" and "h" above.
Figure 2:
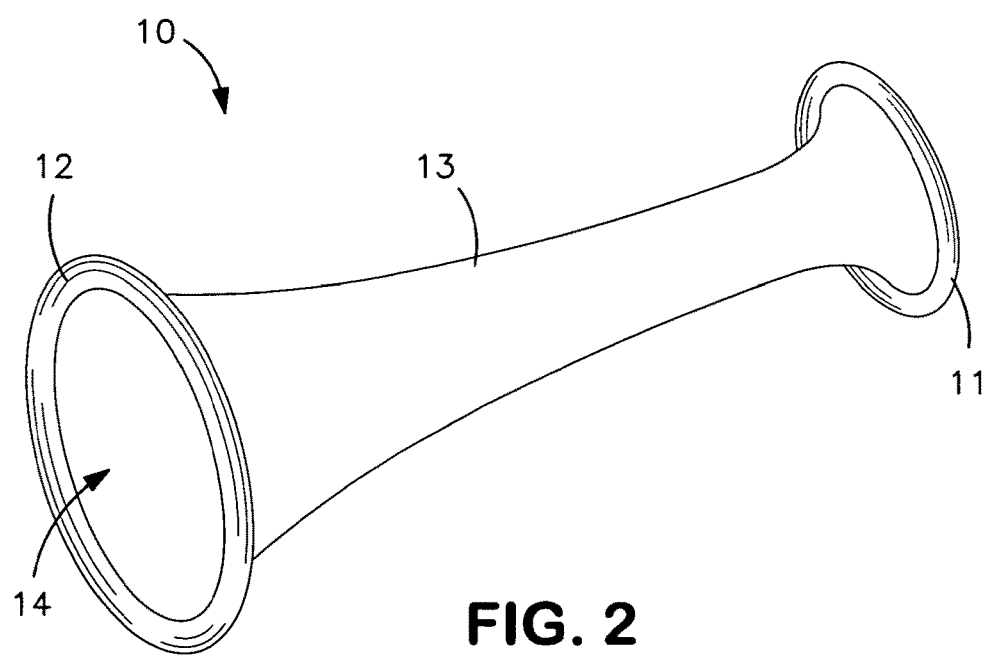
FIG. 2 is a schematic perspective view of a second embodiment of the invention in an "unrolled" condition possessing features described in "e" and "h" above.

Referring to FIGS. 1-4, depicting the first and second embodiments, in which an ostomy appliance 10 may include a seal for sealing around a stoma. The seal may generally comprise an O-ring or similar portion 11 for insertion into the stoma and sealing against the internal wall of the stoma lumen, and a second O-ring or similar portion 12 for sealing and/or restraining against external tissue (skin) or an adhesive component around the stoma. The two O-rings are attached or continuous with a conduit portion or tubular member 13 so as to create a central channel 14 for stoma effluent to pass. The internal O-ring 11 is inserted into the stoma via an insertion tool (not shown) and placed just beyond the abdominal wall (fascia). The external O-ring 12 is then grasped and gently tugged outward to seat the internal O-ring 11 against the fascia. The second external O-ring 12 is then manually "rolled" or twisted using the fingers to roll up the excess length of the tubular member 13 so as to adjust to the specific distance between the fascia and skin. The rolling action occurs in increments utilizing the natural circumferential detent of the O-ring 12. Once sufficient length has been taken up the resistance of the circumferential detent acts to maintain the position of the rolled up length. Additionally, the elastic rebound of the tubular member 13 provides an elastic range to accommodate body movement when the ostomy appliance 10 is worn. The addition of an adhesive on the skin or the adhesive component where the O-ring 12 contacts the skin may aid in securing the ostomy appliance 10. In the first embodiment (FIGS. 1, 3 and 4), the shape of the tubular member 13 is designed to exactly accommodate the diameter reduction resulting from the accumulation of material during the roll up adjustment, resulting in a slightly tapered shape to the tubular member 13 and a somewhat large diameter reduction near the distal end. This will allow for a wide range of fascia-skin adjustment and material elasticity.

In the second embodiment (FIG. 2), the shape of the tubular member 13 is more "trumpet" shaped. This design reduces bunching of the tubular member 13 material in the stoma but will add a radial force to the external O-ring 12 when rolled so the fascia-skin adjustment range may be reduced. This may be compensated for by increasing the external O-ring 12 rigidity and/or decreasing the O-ring 12 diameter and/or increasing the elasticity of the tubular member 13 material. Refinement of this shape will depend on the applicable range of fascia-skin distance for a given ostomy appliance 10 size. Once the ostomy appliance 10 is in place, stoma effluent passes through the central channel 14 and out of the body. If a two piece ostomy pouch system is used in conjunction with the ostomy appliance 10, the chance of effluent leakage should be significantly reduced.

Figure 4:
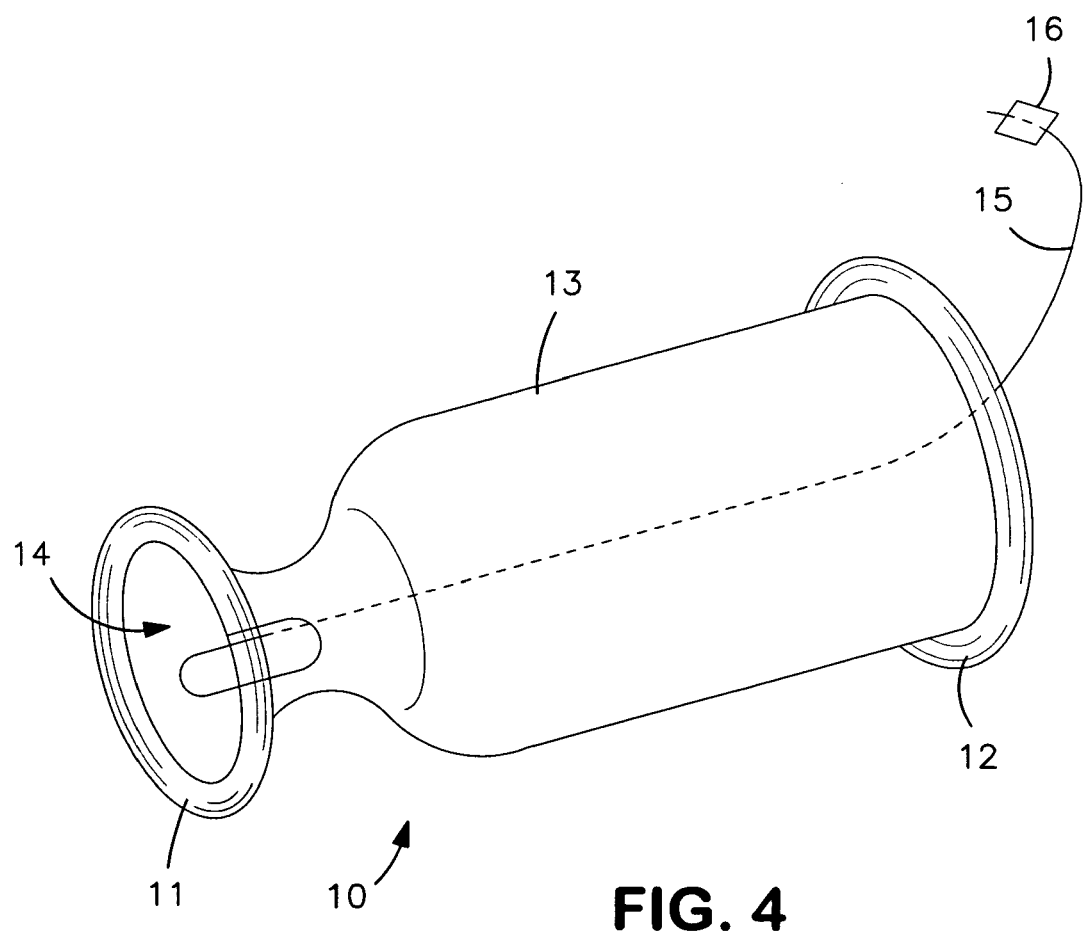
FIG. 4 is a schematic perspective view of the first embodiment of the invention in an "unrolled" condition illustrating the removal string of the device.

To effect easy removal of the ostomy appliance 10 a removal string 15 is attached in a specific way to the internal O-ring 11 (FIG. 4). The removal string 15, comprising of nylon, silk or other suitable material, is driven through and attached to the O-ring 11 from the front (distal side) and exits the back. The removal string 15 is then looped around and run through the central channel 14 where it is suitably adhered to the skin or ostomy wafer above the opening of the central channel 14 by way of an attached adhesive strip 16. When the user wishes to remove the ostomy appliance 10 the removal string 15 is gently pulled. This twists the internal O-ring 11 in a manner that collapses the O-ring shape and allows the O-ring 11 to more easily pass through the stoma opening and out of the body and discarded.

Figure 5:
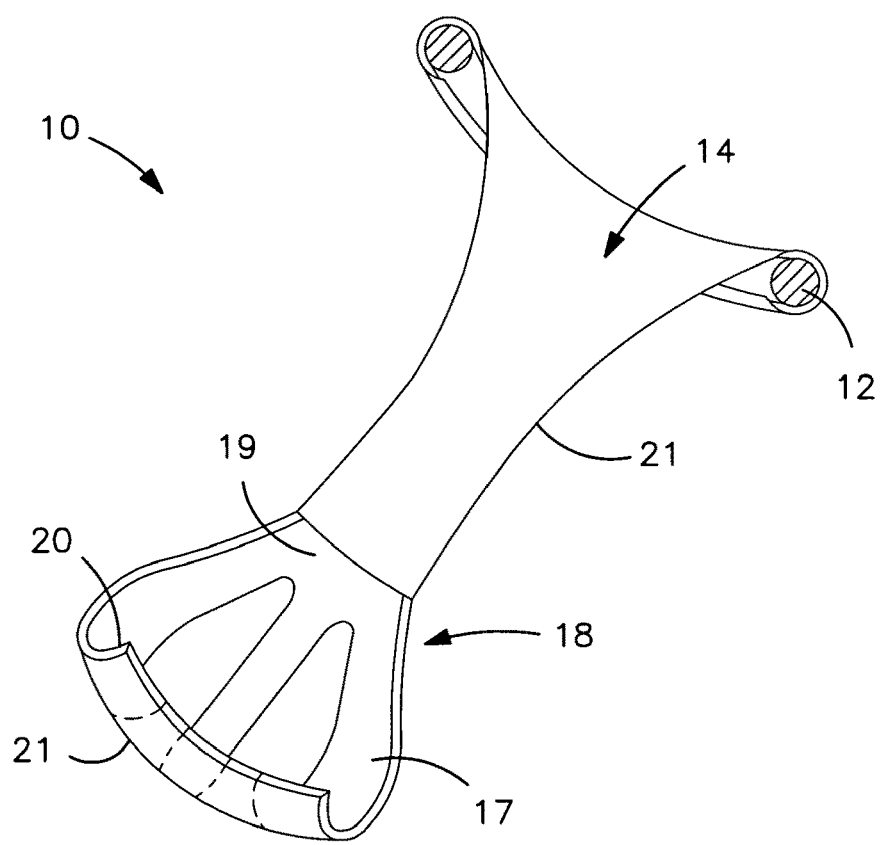
FIG. 5 is a schematic sectional view showing a third embodiment of the invention in an "unrolled" and deployed condition possessing features described in "f" and "h" above.

In a third embodiment of the ostomy appliance 10, referring to FIG. 5, an ostomy appliance 10 may include a seal for sealing around a stoma such that the seal comprising the internal portion for sealing against the internal wall of the stoma lumen consists of a funnel-shaped member 18 possessing finger-like protrusions 17. These protrusions 17 are continuous with a ringed feature 19 at their base that provides support to maintain the opening of the central channel 14 through the funnel-shaped member 18. The dimensions of the protrusions 17 in conjunction with the flexible and/or elastic material properties of the funnel-shaped member 18 are designed so that the member 18 is rigid enough to maintain shape, but flexible and soft enough to bend the protrusions 17 together to achieve a cylindrical shape for the member 18. The ends 20 of the protrusions 17 curve inward with a radius so as to prevent the concentration of force at the ends 20 when contacting the intestinal wall. Over the outside of the funnel-shaped member 18 is formed a thin, continuous, highly elastic covering 21 so as to create a collapsible and stretchable webbing between the protrusions 17 and a sealed central channel 14 from the end of the ringed feature 19. This elastic covering 21 is bonded to or otherwise attached to the funnel-shaped member 18. It may be that the elastic covering 21 is an over-molding, where the protrusions 17 are formed prior to the over-molding in a pre-loaded state, such that during the over-molding process the protrusions 17 are held in tension so that when the completed ostomy appliance 10 is deployed in situ, the webbing portion of the elastic covering 21 retains a stretched condition to maintain the seal to the intestinal wall. The elastic covering 21 which forms the central channel 14 extends through the stoma opening and out of the body when the ostomy appliance 10 is in place. The shape of the elastic covering 21, which forms the central channel 14, is similar to the proximal portion of the tubular member 13 of the second embodiment above (FIG. 2), where the shape of the elastic covering 21 is "trumpet-shaped" and attached to an external O-ring 12, so as to function similarly as an adjustment to the various fascia-skin distances.

Figure 3:
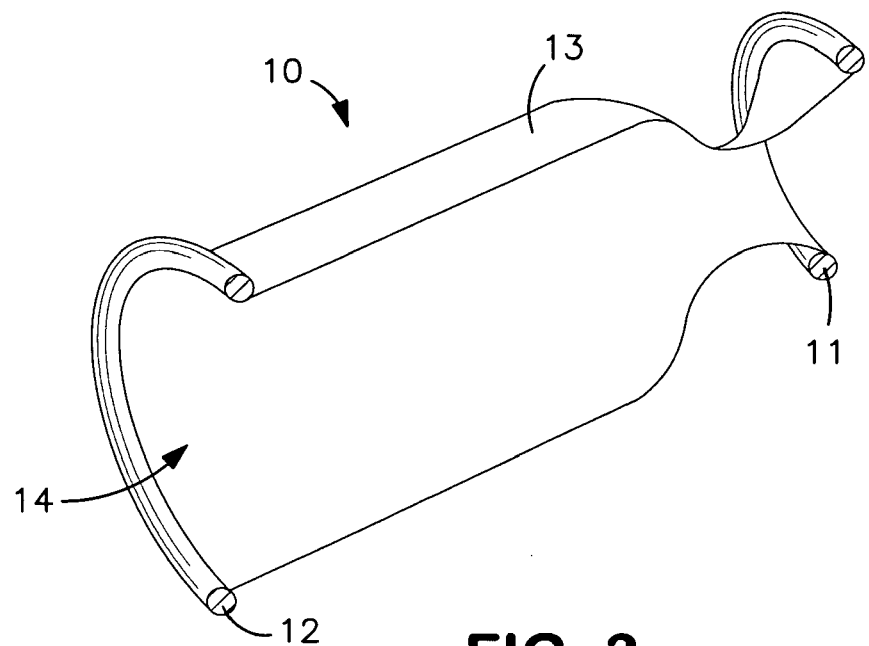
FIG. 3 is a schematic sectional view showing the first embodiment of the invention in an "unrolled" condition.

In another embodiment the shape of the elastic covering 21, which forms the central channel 14 may also be of a tubular tapered shape attached to an external O-ring 12 as in the first embodiment above (FIGS. 1, 3 and 4).

Still another embodiment may have the supporting ringed feature 19 extend in a tubular straight shape through the stoma passageway and out of the body.

The means of inserting the ostomy appliance 10 into the stoma may involve the use of a tubular shaped insertion tool (not shown). The tool is placed through the central channel 14 from the proximal end of the ostomy appliance 10, passes through the ringed feature 19, and the tool end engages the curved ends of the protrusions 17 when they are bent together into a cylindrical shape. The tool may be held in place by adhesive and/or engaging features at the tool end. The protrusions 17 may also possess adhesive and/or engaging features. The tool may also be held in place via a feature that maintains a fit with the ringed feature 19 and/or the proximal end of the tool and ostomy appliance 10. The insertion tool may be fixed in place at manufacture and packaged to facilitate user insertion.

The third embodiment of the ostomy appliance 10 is inserted into the stoma opening via the insertion tool and the tool is then disengaged and removed, allowing the shape memory of the funnel-shaped member 18 to deploy the ostomy appliance 10 and create a seal against the intestinal wall. As with the first and second embodiments the external O-ring 12 is then grasped and manually "rolled" or twisted using the fingers to roll up the excess length of the elastic covering 21, which forms the central channel 14, so as to adjust to the specific distance between the fascia and skin. The elastic rebound of the elastic covering 21, which forms the central channel 14, also provides an elastic range to accommodate body movement when the ostomy appliance 10 is worn. The addition of an adhesive on the skin or on an adhesive component where the external O-ring 12 contacts, may aid in securing the ostomy appliance 10.

The shape memory of the funnel-shaped member 18 is measured so that the force required to simply pull the ostomy appliance 10 out of the stoma is such that it does not inflict tissue damage and is comfortable to the user.

Figure 6:
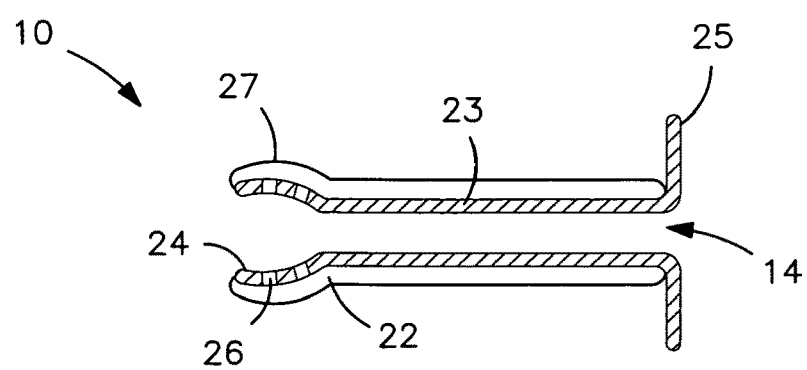
FIG. 6 is a schematic sectional view showing a fourth embodiment of the invention possessing features described in "m" above.

In a fourth embodiment of the ostomy appliance 10, referring to FIG. 6, an ostomy appliance 10 may include a seal for sealing around a stoma such that the seal comprising the internal portion for sealing against the internal wall of the stoma lumen consists of an expandable foam material 22. This foam material 22 covers the exterior of a more rigid central support 23 that is of a generally tubular shape, but having a semi-spherical bulge 24 at the distal end and flange-like feature 25 at the proximal end. The foam material 22 may have varying thicknesses over different portions of the central support 23, e.g., it may be thicker over the semi-spherical bulge 24. The foam material 22 expands significantly in the presence of moisture. Over the exterior of the foam material 22 may be a coating or covering of very thin, elastic sealing film 27. The flange-like feature 25 remains exterior to the body when the ostomy appliance 10 is in place so as to be clear of the stoma, and may attach to the skin, an external wafer or other component. The flange-like feature 25 may be shaped generally flat, convex, concave or a combination of these. Through the semi-spherical bulge 24 are a series of holes 26 for allowing moisture to pass through the central support 23. There may be additional holes 26 at other points along the central support 23.

The ostomy appliance 10 may be manually inserted through the aperture of a two-piece ostomy wafer and into the stoma and the flange-like feature 25 may then attach to the wafer. The moisture and liquid effluent in the stoma pass into the central channel 14 and through the holes 26 in the central support 23 and into the foam material 22 causing the foam material 22 to expand, stretching the sealing film 27 and creating a seal against the intestinal wall.

The ostomy appliance 10 is removed manually by detaching the ostomy appliance 10 from the ostomy wafer and pulling it out of the stoma and discarded.

Figure 7A:
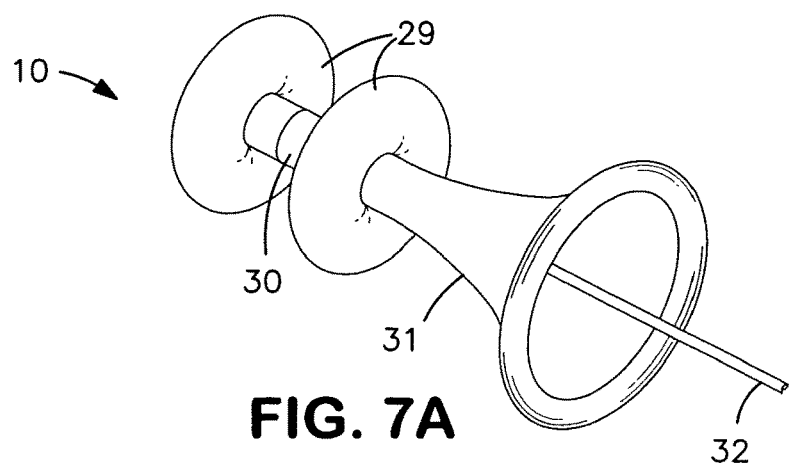
FIG. 7a is a schematic perspective view showing a fifth embodiment of the invention in an "unrolled" and inflated condition possessing features described in "g" and "h" above.
Figure 7B:
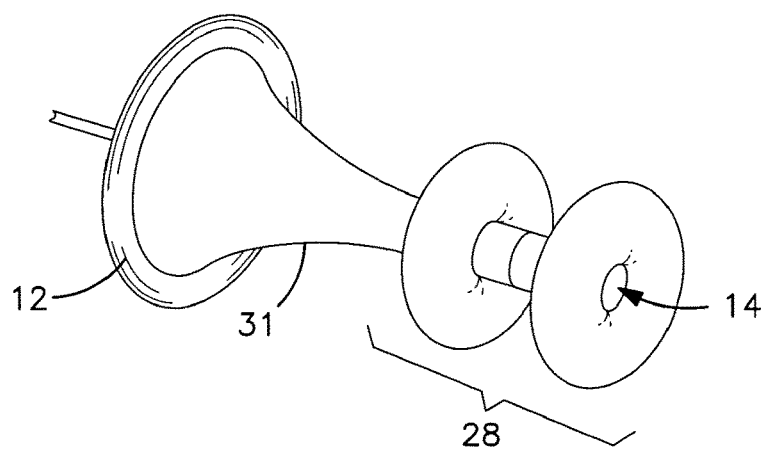
FIG. 7b is complementary schematic perspective views to FIG. 7a showing a fifth embodiment of the invention in an "unrolled" and inflated condition possessing features described in "g" and "h" above.
Figure 8:
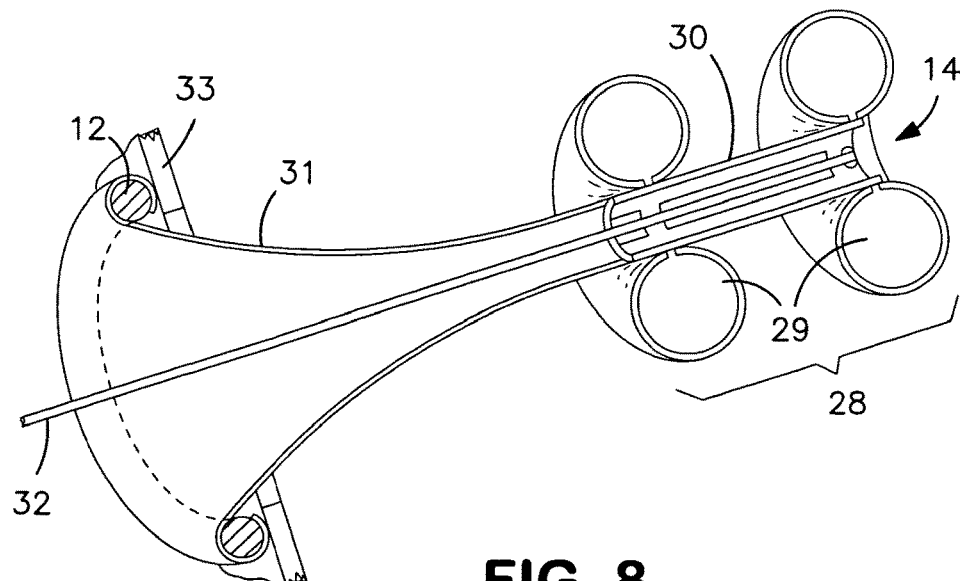
FIG. 8 is a schematic sectional view showing the fifth embodiment of the invention in an "unrolled" and inflated condition.

In a fifth embodiment of the ostomy appliance 10, referring to FIGS. 7 and 8, an ostomy appliance 10 may include a seal for sealing around a stoma such that the seal comprising the internal portion for sealing against the internal wall of the stoma lumen consists of an internally inflated chamber portion 28 that may be constructed of dual interconnecting chambers 29 attached and/or bonded to, or constructed of one formed shape, with a tubular more firm or rigid central member 30. The inflated chamber portion 28 may be attached to another more elastic tubular member 31 similar to the proximal portion of the tubular member 13 of the second embodiment above (FIG. 2), where the shape of the elastic tubular member 31 is "trumpet-shaped" and attached to an external O-ring 12, so as to function similarly as an adjustment to the various fascia-skin distances. In another embodiment the shape of the elastic tubular member 31, which also forms part of the central channel 14, may also be of a tubular tapered shape attached to an external O-ring 12 as in the first embodiment above (FIGS. 1, 3 an 4).

The inflated chamber portion 28 of the fifth embodiment of the ostomy appliance 10 is inserted fully behind the fascia. The proximal end of the ostomy appliance 10, which includes a portion of the elastic tubular member 31 and the attached O-ring 12, remains external to the stoma. The dual interconnecting chambers 29 are then inflated via an inflation tube 32 that has a check valve, and an inflation device such as a syringe. Once inflated, as with previous embodiments, the external O-ring 12 is then grasped and gently tugged outward to seat the most proximal of the dual interconnecting chambers 29 against the fascia. The external O-ring 12 is then manually rolled so as to adjust to the specific distance between the fascia and skin. The firmness of the external O-ring 12 acts to maintain the position of the rolled up length and the elastic rebound of the tubular member 31 provides an elastic range to accommodate body movement when the ostomy appliance 10 is worn. Also, as with previous embodiments, the addition of an adhesive on the skin or the adhesive component 33 where the O-ring 12 contacts may aid in securing the ostomy appliance 10. This assembly configuration may allow for easy insertion into the stoma opening without the need for an insertion device.

The ostomy appliance 10 is removed by deflating the interconnecting chambers 29 and pulling the ostomy appliance 10 out of the body and discarded.

Figure 9:
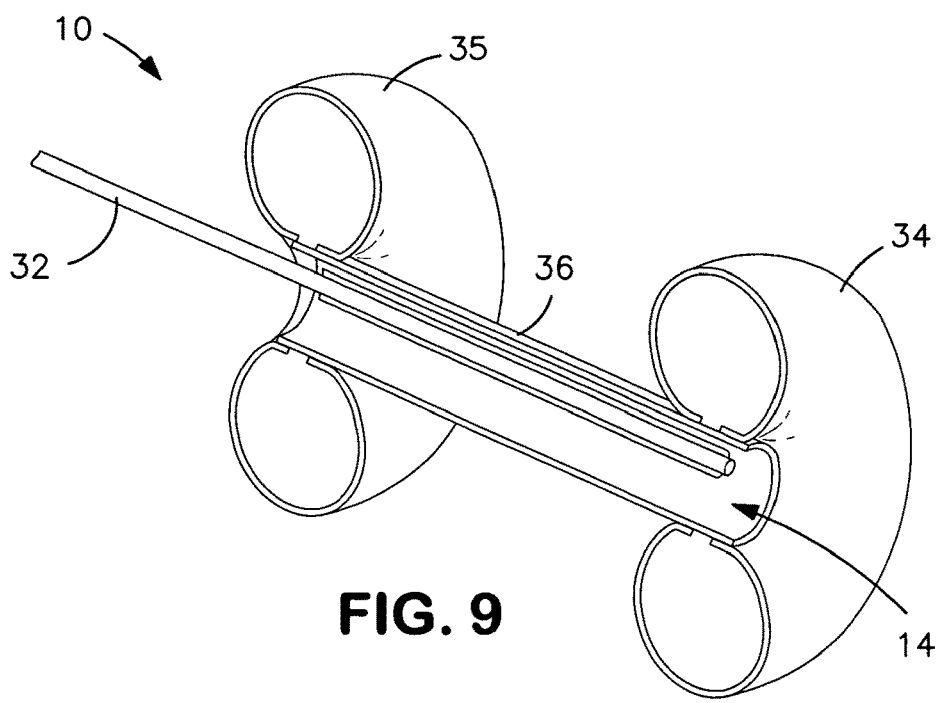
FIG. 9 is a schematic sectional view a sixth embodiment of the invention in an inflated condition possessing features described in "b" and "g" above.

In a sixth embodiment of the ostomy appliance 10, referring to FIG. 9, an ostomy appliance 10 may include a seal for sealing around a stoma such that the seal comprising the internal portion for sealing against the internal wall of the stoma lumen consists of an internal inflated chamber 34 and an external portion for restraining against external tissue consisting of an external inflated chamber 35 that may be fluidically interconnected and attached and/or bonded to, or constructed of one formed shape, with a tubular more firm or rigid central member 36.

The internal chamber 34 and the portion of the central member 36, up to just before the external chamber 35, of the ostomy appliance 10 is inserted into the stoma. The interconnected chambers, 34, 35, are then inflated via an inflation tube 32 that has a check valve, and an inflation device.

The ostomy appliance 10 is removed by deflating the interconnected chambers, 34, 35 and pulling the ostomy appliance 10 out of the body and discarded.

Figure 10:
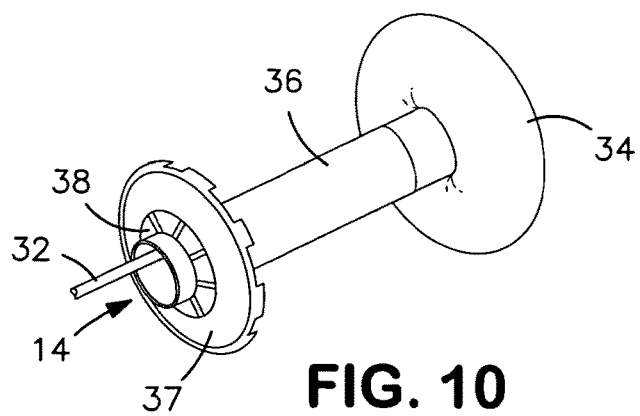
FIG. 10 is a schematic perspective view showing a seventh embodiment of the invention in an inflated condition possessing features described in "g", "j" and "k" above.

In a seventh embodiment of the ostomy appliance 10, referring to FIG. 10, an ostomy appliance 10 may include a seal for sealing around a stoma such that the seal comprising the internal portion for sealing against the internal wall of the stoma lumen consists of a internal inflated chamber 34 attached and/or bonded to, or constructed of one formed shape, with a tubular more firm or rigid central member 36. The central member 36 continues outside the body, so as to provide a passageway through the ostomy appliance 10. The member external to the stoma may be comprised of a more rigid material, effectively a collar 37, and may possess features along the contacting surface with the central member 36 such that the collar 37 may be manually placed over and easily slid down the central member 36 but will meet more resistance moving up the central member 36. This may be accomplished via angled, bendable protrusions 38 with sharp ends extending radially inward and contacting the central member 36 so that movement in one direction (downward or distally) is facilitated but opposite movement (upward or proximally) is restrained. The restrained movement in the proximal direction of the collar 37 may not be a rigid stop but measured so as to prevent tissue damage in the event of excessive or unexpected body movement. Another embodiment may involve a locking feature (not shown) within the collar 37 whereas once the collar 37 is in place over the central member 36 a second component of the collar 37 interacts to squeeze the central member 36 sufficiently so as to hold the collar 37 in its position on the central member 36. The collar 37 shape is such as to be clear of the stoma, and may attach to the skin, an external wafer or other component. The collar 37 may be shaped generally flat, convex, concave or a combination of these. The collar 37 may not comprise an external seal but may only rest or attach and have "vents" allowing fluid escape in the event the internal seal to the intestine is compromised. The effluent venting may prevent occlusion of the stoma opening in the event of seal failure. The effluent venting may also be an indicator that the device is in need of replacement.

The internal chamber 34 and the portion of the central member 36 of the ostomy appliance 10 is inserted into the stoma and fully behind the fascia and inflated via an inflation tube 32 that has a check valve, and an inflation device. The central member 36 is then gently tugged in the proximal direction to seat the internal chamber 34 against the fascia. The collar 37 is then placed over the central member 36 and slid down to rest against the skin, an external wafer or other component, then if needed locked in place. The central member 36 may have excess length trimmed to reduce the profile of the ostomy appliance 10.

The ostomy appliance 10 is removed by deflating the internal chamber 34 and pulling the ostomy appliance 10 out of the body and discarded.

Figure 11:
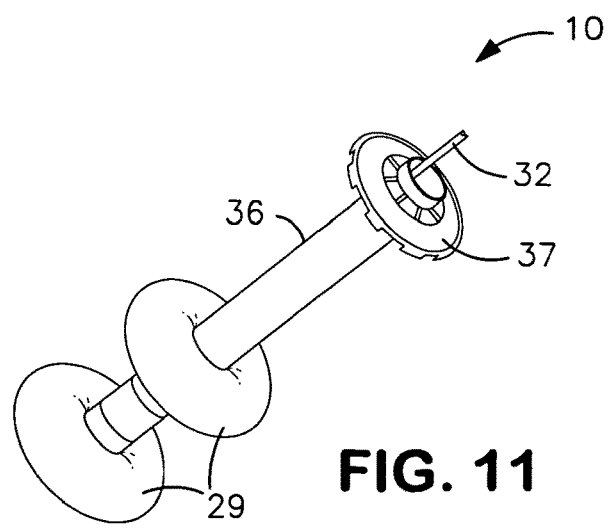
FIG. 11 is a schematic perspective view showing an eighth embodiment of the invention in an inflated condition possessing features described in "g", "j" and "k" above.

The eighth embodiment of the ostomy appliance 10, referring to FIG. 11, has the same features and function as the seventh except there are dual interconnecting chambers 29 similar to the fifth embodiment.

Figure 12A:
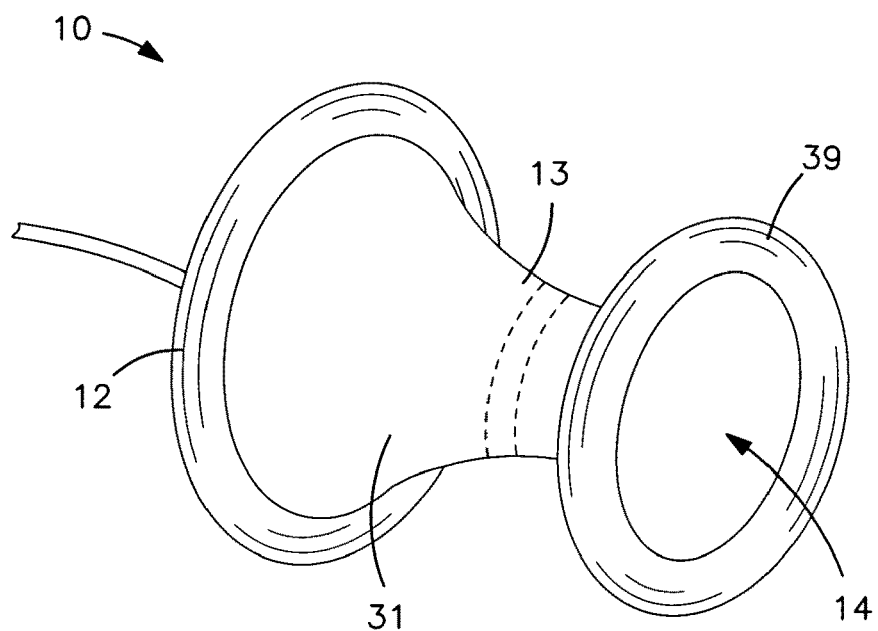
FIG. 12a is a schematic perspective view showing an ninth embodiment of the invention in an "unrolled" and inflated condition possessing features described in "a" and "h" above.
Figure 12B:
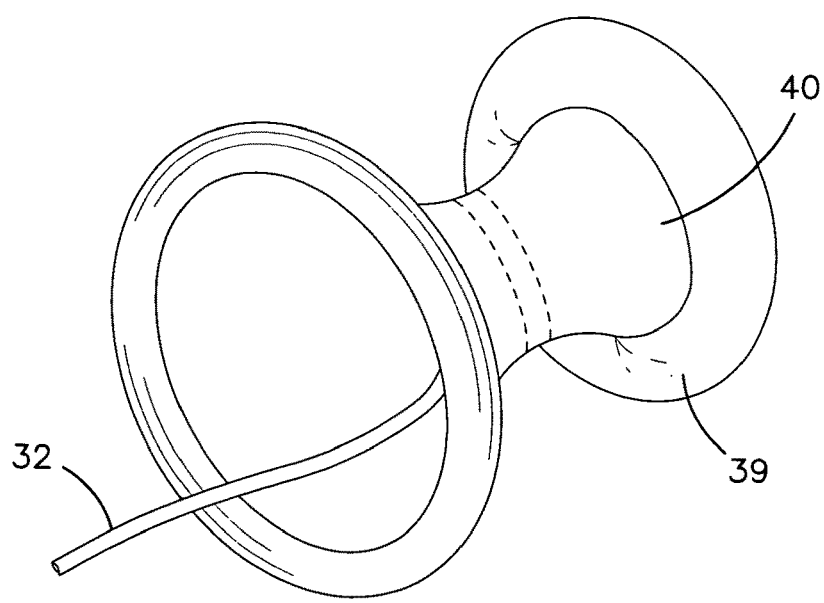
FIG. 12b is a complementary schematic perspective view to FIG. 12a showing an ninth embodiment of the invention in an "unrolled" and inflated condition possessing features described in "a" and "h" above.
Figure 13:
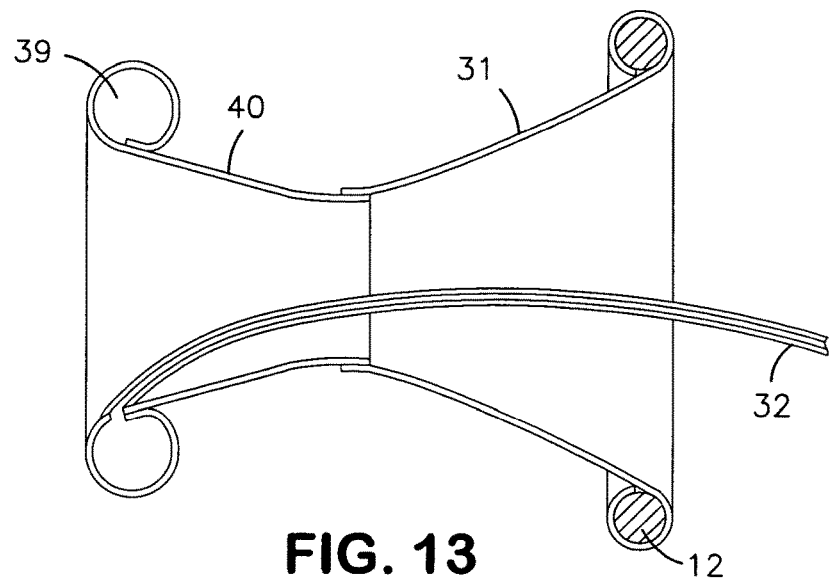
FIG. 13 is a schematic sectional view showing the ninth embodiment of the invention in an "unrolled" and inflated condition.
Figure 14A:
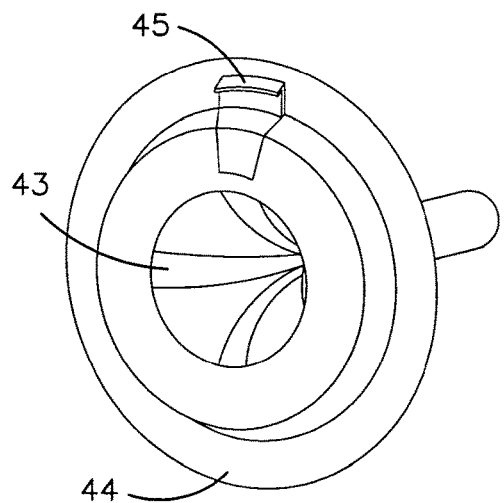
FIG. 14a is a schematic perspective views showing a tenth embodiment of the invention in an un-deployed condition possessing features described in "a" and "i" above (but cannot be rolled).
Figure 14B:
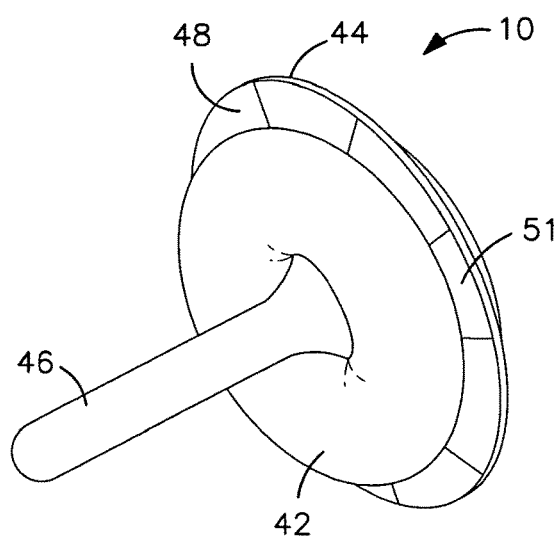
FIG. 14b is a complementary schematic perspective view to FIG. 14a showing a tenth embodiment of the invention in an un-deployed condition possessing features described in "a" and "i" above (but cannot be rolled).
Figure 15:
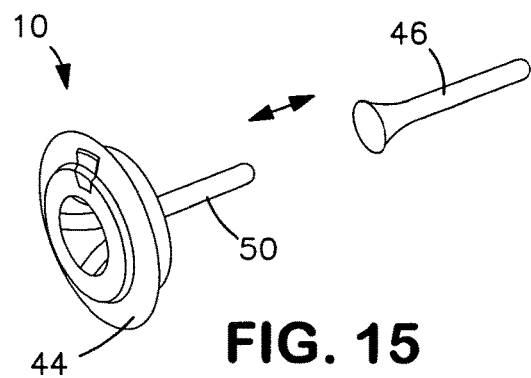
FIG. 15 is a schematic perspective view showing the tenth embodiment of the invention having the constraining cap removed.
Figure 16:
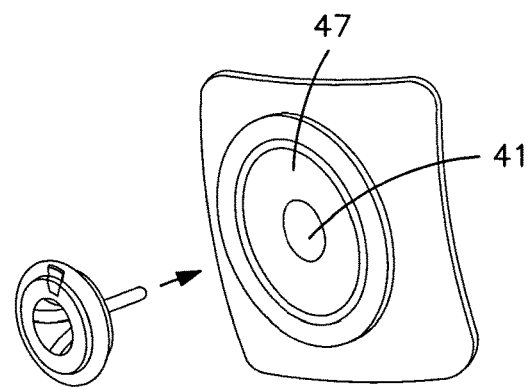
FIG. 16 is a schematic perspective view showing the tenth embodiment of the invention being inserted into the stoma through a two piece ostomy wafer.
Figure 17:
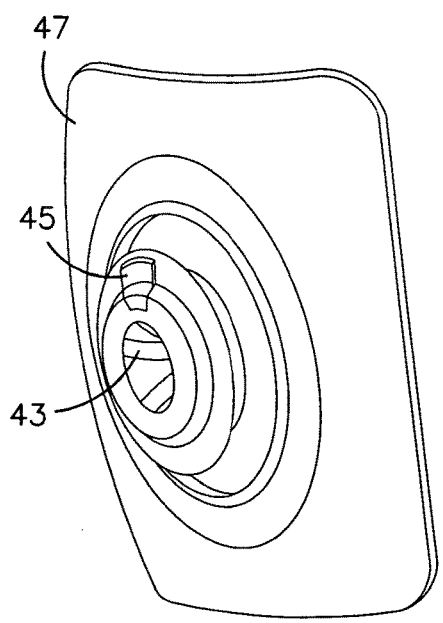
FIG. 17 is a schematic perspective view showing the tenth embodiment of the invention inserted in the stoma through a two piece ostomy wafer but not yet deployed.
Figure 18:
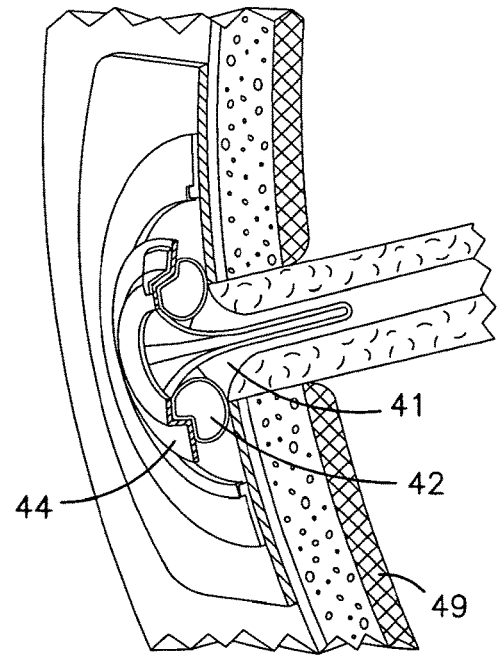
FIG. 18 is a schematic sectional view showing the tenth embodiment of the invention inserted in the stoma through a two piece ostomy wafer but not yet deployed.
Figure 19:
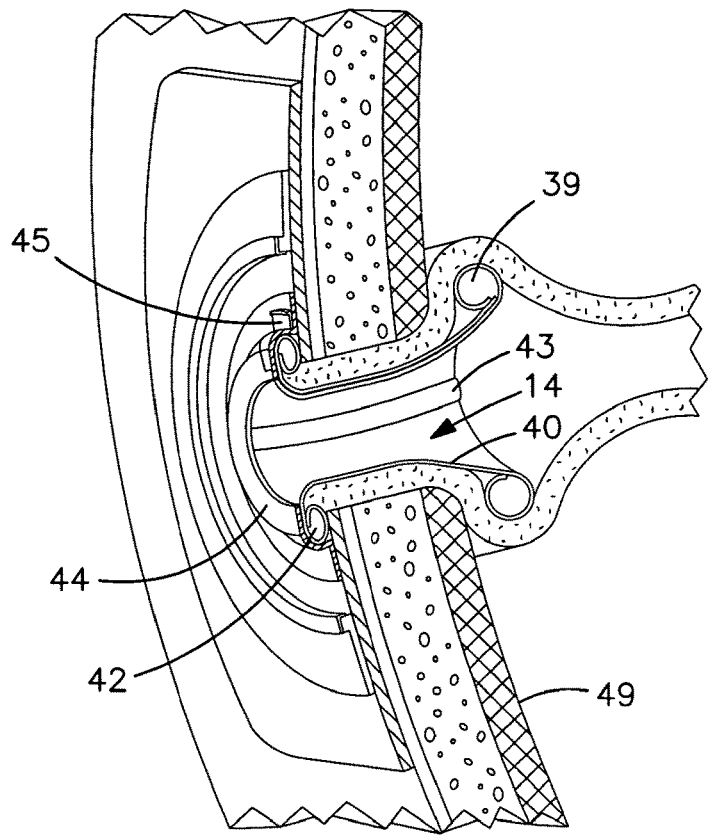
FIG. 19 is a schematic sectional view showing the tenth embodiment of the invention inserted in the stoma through a two piece ostomy wafer and deployed.
Figure 20:
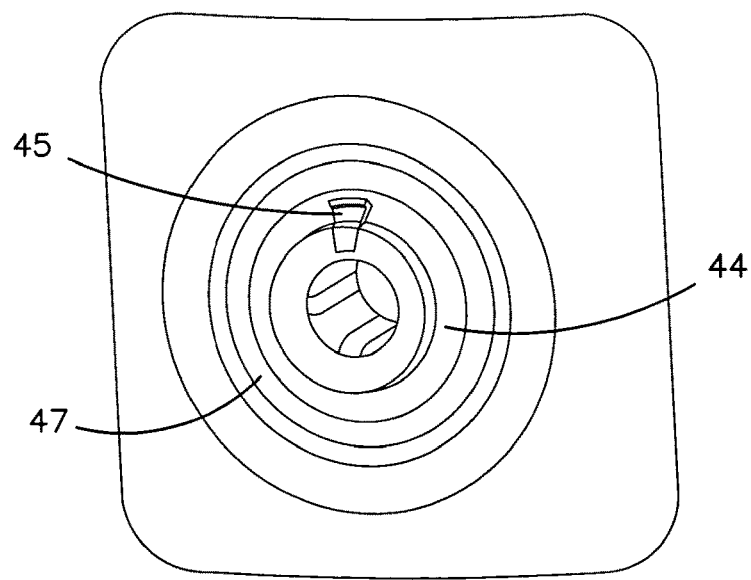
FIG. 20 is a schematic front perspective view showing the tenth embodiment of the invention inserted in the stoma through a two piece ostomy wafer and deployed.

In a ninth embodiment of the ostomy appliance 10, referring to FIGS. 12 and 13, an ostomy appliance 10 may include a seal for sealing around a stoma such that the seal comprising the internal portion for sealing against the internal wall of the stoma lumen consists of an inflatable chamber 39 toroidal in shape and sealed to or continuous with a tubular tapered or "trumpet-shape" central channel 40 constructed of a thin elastic material. The tapered channel 40 may be attached to another elastic tubular member 31 similar to the proximal portion of the tubular member 13 of the second embodiment above (FIG. 2), where the shape of the elastic tubular member 31 is "trumpet-shaped" and attached to an external O-ring 12, so as to function similarly as an adjustment to the various fascia-skin distances. In another embodiment the shape of the elastic tubular member 31, which also forms part of the central channel 14, may also be of a tubular tapered shape attached to an external O-ring 12 as in the first embodiment above (FIGS. 1, 3 and 4). The distal end of the ostomy appliance 10, including the inflatable chamber 39, the distal end of the inflation tube 32 and the tapered channel 40 with a portion of the elastic tubular member 31 may be constrained, e.g., folded, rolled and/or twisted, into a thin, long shape to ease insertion into the stoma without the need for an insertion tool. Gelatine or other coating on the constrained members may facilitate insertion by maintaining the constraint until the gelatine contacts or is within the moist interior of the stoma. The addition of a cap over the internal chamber may also aid in maintaining the chamber in a constrained condition before use.

The constrained distal end of the ninth embodiment of the ostomy appliance 10 is inserted fully into the stoma, so as the end is behind the fascia. The proximal end of the ostomy appliance 10 which includes a portion of the elastic tubular member 31 and the attached O-ring 12 remain external to the stoma. After the constraining coating has dissolved, the inflatable chamber 39 is then inflated via an inflation tube 32 that has a check valve, and an inflation device such as a syringe. Once inflated, as with previous embodiments, the external O-ring 12 is then grasped and gently tugged outward (proximally) to seat the inflatable chamber 39 against the fascia. The external O-ring 12 is then manually rolled so as to adjust to the specific distance between the fascia and skin. The firmness of the external O-ring 12 acts to maintain the position of the rolled up length, and the elastic rebound of the tubular member 31 and the tapered channel 40 provides an elastic range to accommodate body movement when the ostomy appliance 10 is worn. Also, as with previous embodiments, the addition of an adhesive on the skin or the adhesive component where the O-ring 12 contacts may aid in securing the ostomy appliance 10.

The ostomy appliance 10 is removed by deflating the inflatable chamber 39 and pulling the ostomy appliance 10 out of the body and discarded.

In a tenth embodiment of the ostomy appliance 10, referring to FIGS. 14, 15, 16, 17, 18, 19 and 20, an ostomy appliance 10 may include a seal for sealing around a stoma 41 such that the seal comprising the internal portion for sealing against the internal wall of the stoma lumen consists of an internal inflatable chamber 39 toroidal in shape and sealed to or continuous with a tubular tapered or "trumpet-shape" central channel 40 constructed of a thin elastic material. The tapered channel 40 may also be continuous with another external inflatable chamber 42 having thicker and/or stronger (less soft) elastic material. There are interconnecting fluid passageways 43 between the internal chamber 39 and the external chamber 42. At the entrance, exit or along the fluid passageways 43 there may be an orifice or other fluid restriction, or valve to delay and/or control the initiation of the fluid transfer from the external chamber 42 to the internal chamber 39. The external chamber 42 is to be pressurized with fluid at manufacture or at some time previous to use, such that the pressure contained, when released, can be utilized to transfer, via elastic action, the fluidic component from the external chamber 42 through the fluid passageways 43 into the internal chamber 39 so the internal chamber 39 may deploy within the body without the need of a secondary component for inflating the ostomy appliance 10. The internal chamber 39 and the tapered channel 40 may be constrained, e.g., folded, rolled and/or twisted, into a thin, long shape to ease insertion into the stoma 41 without the need for an insertion tool. Gelatine or other coating 50 on the constrained members may facilitate insertion by maintaining the constraint until the gelatine contacts or is within the moist interior of the stoma 41. The addition of a cap 46 over the internal chamber 39 and constrained members may also aid in maintaining the internal chamber 39 in a constrained condition before use. Constraining the internal chamber 39 may also prevent premature fluid transfer from the pressurized external chamber 42. Attached to the external chamber 42 is an attachment cover member 44. The function of the cover member 44 is to provide a means of easily handling, attaching/removing and deflating the ostomy appliance 10 and is constructed of a relatively rigid polymer material. On the underside of the cover member 44 along the outer flange is a ring-shaped area 48 that once the ostomy appliance 10 is deployed will contact the surface around the stoma 41 on a two-piece ostomy wafer 47. The ring-shaped area 48 has alternating shallow vents 51 or spaced clearances around the perimeter to allow effluent and/or gas escape from around the back side of the internal seal in the event of seal failure. This ring-shaped area 48 may be coated with an adhesive between the vents 51 and/or the ostomy wafer 47 may have an adhesive for attaching the ostomy appliance 10. Additionally, within the cover member 44 is a deflation tear-away tab 45 used to deflate the ostomy appliance 10. The deflation tab 45 is a break-away feature of the cover member 44 in that the attachment or bonding of the material of the external chamber 42 to the attachment member 44 overlaps the perforation of the deflation tab 45 such that when the deflation tab 45 is broken, the seal to the external chamber 42 is compromised, deflating the ostomy appliance 10. Successfully packaging the ostomy appliance 10 may be accomplished by utilizing a container pressurized with the same fluid and to the same pressure as the external chamber 42 in the non-deployed state. This may alleviate the problem of the ostomy appliance 10 depressurizing over time due to the permeability of the ostomy appliance 10 materials. The package container may be constructed of barrier films or may be a hard polymer or an aluminum (e.g., like a soda can) or other container that will hold the fluidic pressure over time until the contained ostomy appliance 10 is needed.

The tenth embodiment of the ostomy appliance 10 is removed from its container, the cap 46 is removed (FIG. 15), and the ostomy appliance 10 is inserted fully into the stoma 41 (FIGS. 16, 17 and 18), so as the end of the constrained portion is behind the fascia 49. The constraining coating 50 dissolves and the transfer of fluid from the external chamber 42 to the internal chamber 39 initiates. Applying a manual downward pressure to the cover member 44 may also initiate and/or accelerate the transfer of fluid. The internal chamber 39 is then inflated, and the external chamber 42 deflated which allows the ring-shaped area 48 to contact the surface of the ostomy wafer 47 and attach the ostomy appliance 10. Stoma effluent is then free to flow through the ostomy appliance 10 and out into a pouch without contacting other tissue.

The ostomy appliance 10 is removed by pulling the deflation tab 45 out, deflating the ostomy appliance 10, then pulling the ostomy appliance 10 away from the ostomy wafer 47 and out of the body and discarded.

Figure 21:
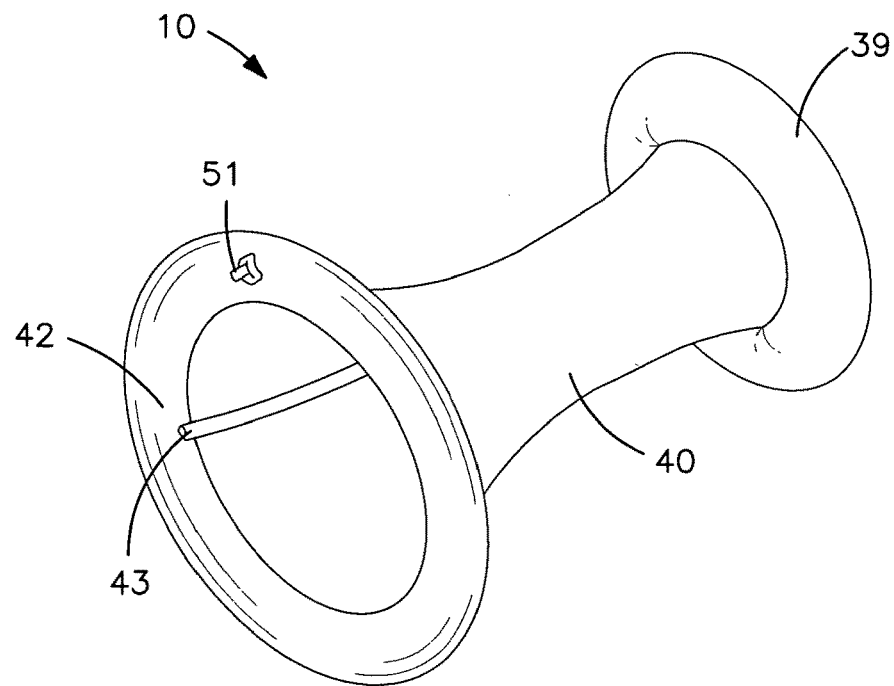
FIG. 21 is a schematic perspective view showing an eleventh embodiment of the invention in an "unrolled" and inflated condition possessing features described in "a" and "i" above (can be rolled).
Figure 22:
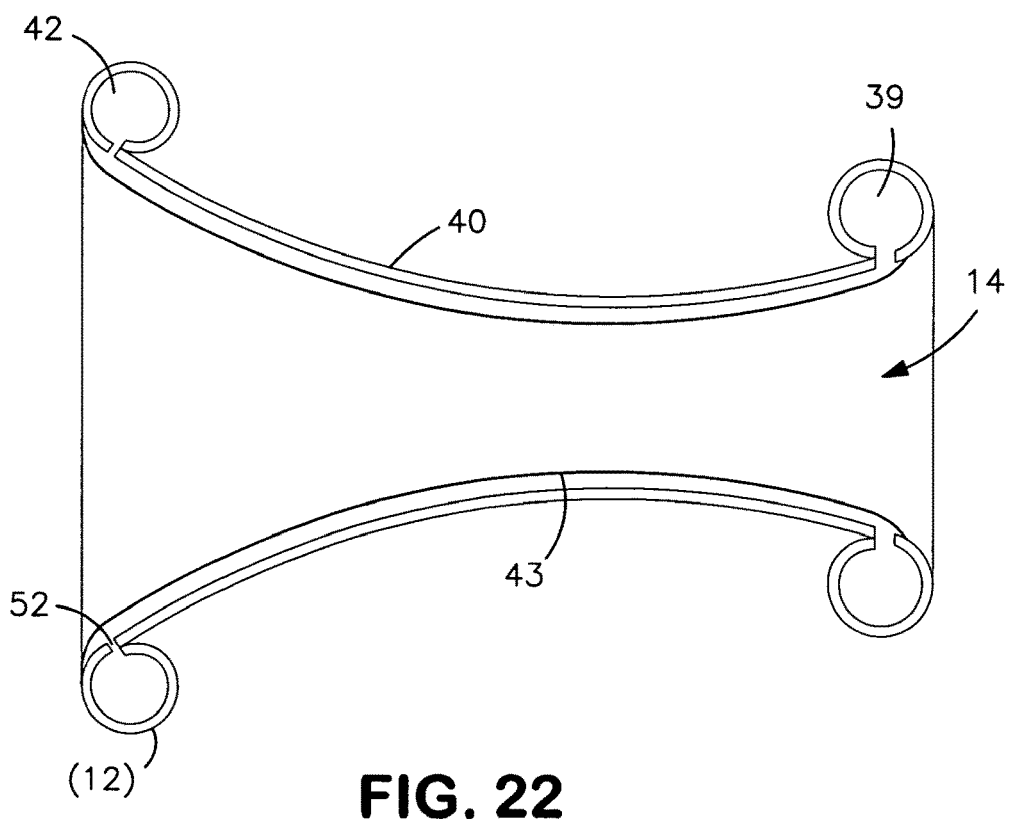
FIG. 22 is a schematic sectional view showing the eleventh embodiment of the invention in an "unrolled" and inflated condition.

The eleventh embodiment of the ostomy appliance 10, referring to FIGS. 21 and 22, has the same features and functionality as the tenth except does not possess an attachment cover member 44 but instead relies on the external inflatable chamber 42 for providing a means of easily handling, attaching/removing and deflating the ostomy appliance 10. As with the tenth embodiment there are interconnecting fluid passageways 43 between the internal chamber 39 and the external chamber 42 that contains an orifice 52 or other fluid restriction, or valve to delay and/or control the initiation of the fluid transfer from the external chamber 42 to the internal chamber 39. As with the tenth embodiment, the external chamber 42 is to be pressurized with fluid at manufacture or at some time previous to use. The contained pressurized fluid, when released, may transfer, via elastic action, the fluid from the external chamber 42 through the orifice(s) 52 and fluid passageways 43 into the internal chamber 39 so the internal chamber 39 may deploy within the body without the need of a separate inflation device. The internal chamber 39 and the tapered channel 40 may also be constrained and held via a coating 50, as with the tenth embodiment, into a thin, long shape to ease insertion into the stoma 41. A cap may be placed over the internal chamber 39 and constrained members. Additionally, once the ostomy appliance 10 is in place and the external chamber 42 has transferred the fluid into the internal chamber 39 to deploy the ostomy appliance 10, the deflated external chamber 42 may then be used, being now similar to the external O-ring 12 in the ninth embodiment (FIGS. 12 and& 13), to function as an adjustment to the various fascia-skin distances via a circumferential roll up of the tapered channel 40. Successfully packaging the ostomy appliance 10 may be accomplished similar to the tenth embodiment, by utilizing a container pressurized with the same fluid and to the same pressure as the external chamber 42 in the non-deployed state.

Figure 23:
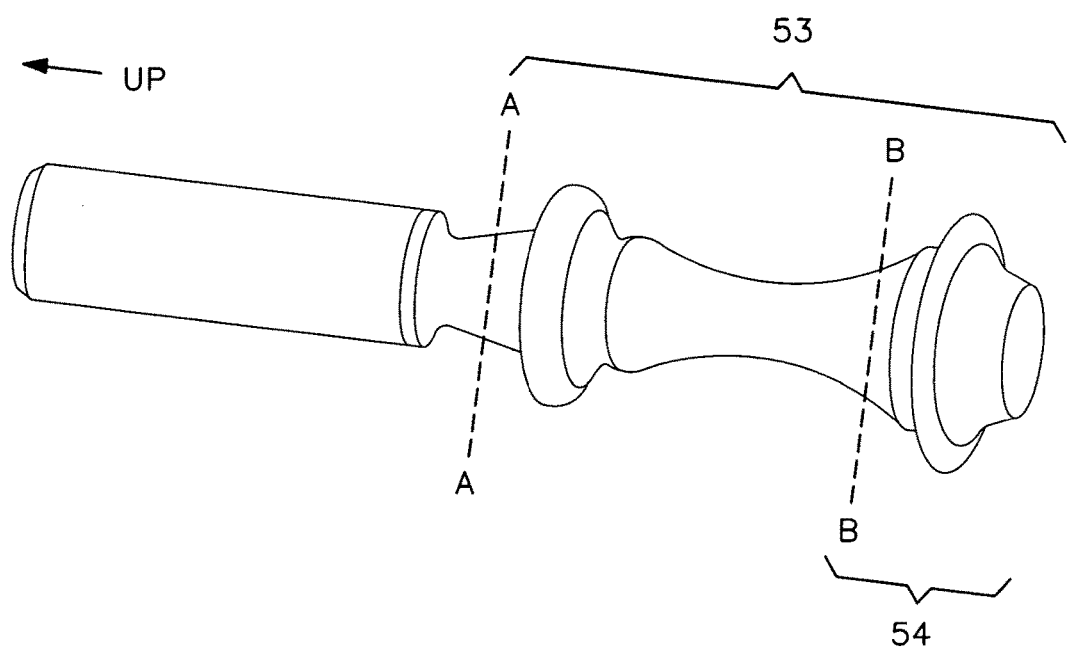
FIG. 23 is a schematic perspective view showing an example dip-molding tool for creating the eleventh embodiment of the invention.

The ostomy appliance 10 may be fabricated in part by means of a dip molding process. FIG. 23 demonstrates an example of a possible dip-mold mandrel tool. First the tool may be dipped in an appropriate material component up to the A-A line and allowed to cure so as to form a thin, soft, highly elastic film for the formation of the internal chamber 39 and tapered channel 40. This defines the first dipping area 53. Then the tool may be dipped in an appropriate material component up to the B-B line and allowed to cure so as to form a thick, strong, elastic film for the formation of the external chamber 42. This defines the second dipping area 54. The second dipping area 54 may require subsequent dips to achieve the desired thickness. After curing of the dip-mold materials additional assembly steps will be needed to complete the ostomy appliance 10.

The eleventh embodiment of the ostomy appliance 10, very similar to the tenth, is removed from its container, the cap over the constrained members is removed, and the ostomy appliance 10 is inserted fully into the stoma 41, so as the end of the constrained portion is behind the fascia 49. The constraining coating dissolves and the transfer of fluid from the external chamber 42 to the internal chamber 39 initiates. The internal chamber 39 is then inflated, and the external chamber 42 deflated which allows the deflated external chamber 42 to be used as the external O-ring 12 as in previous embodiments. The external chamber 42 is grasped and gently tugged outward (proximally) to seat the inflatable chamber 39 against the fascia 49. The external chamber 42 is then manually rolled so as to adjust to the specific distance between the fascia and skin. The firmness of the deflated external chamber 42 acts to maintain the position of the rolled up length, and the elastic rebound of the tapered channel 40 provides an elastic range to accommodate body movement when the ostomy appliance 10 is worn. Adhesive on the surface of the ostomy wafer 47 contacting the underside of the external chamber 42 assists in attaching the ostomy appliance 10. Stoma effluent is then free to flow through the ostomy appliance 10 and out into a pouch without contacting other tissue.

The ostomy appliance 10 is removed by pulling the deflation pull-out 51, deflating the ostomy appliance 10, then pulling the ostomy appliance 10 away from the ostomy wafer 47 and out of the body and discarded.

It will be appreciated that the foregoing description contains preferred forms of the invention, and that many modifications, improvements and equivalents are within the scope of the claimed invention.

I claim:

1. A stoma extender comprising:
   a first end for insertion into a stoma for diverting stomal effluent into the stoma extender before the effluent exits the stoma;
   a second end constructed of a toroidal-shaped elastic material or O-ring for remaining external of the stoma, for providing a discharge exit for stomal effluent; and
   an elastic conduit portion coupled between the first and second ends for communicating stomal effluent through the stoma extender, wherein the length of the conduit portion is adjustable stably to permit adaptation of the stoma extender to an individual's stoma, wherein the diameter of the first end of the stoma extender is smaller than the diameter of the second end of the stoma extender, and the conduit portion has a tapered shape from the second end to the first end permitting at least partial rolling-up of the second end of the conduit portion along its axis to reduce the length and at least partial unrolling of the second end of the conduit portion along its axis to increase the length utilizing the circumferential detent of the toroidal shaped elastic material or O-ring of the second end; and wherein the diameter of the first end remains smaller than the diameter of the second end during the at least partial rolling-up of the second end and diversion of the stomal effluent.

2. The stoma extender of claim 1, wherein the conduit portion is rollable from the second end to permit adaptation of the length once the first end is already inserted into the stoma.

3. The stoma extender of claim 1, wherein at least a portion of the conduit portion is configured to permit at least one selected from: at least partial folding-back of the conduit portion along its axis to reduce the length and at least partial unfolding of a folded-back portion of the conduit portion along its axis to increase the length.

4. The stoma extender of claim 3, wherein the conduit portion is foldable from the second end to permit adaptation of the length once the first end is already inserted into the stoma.

5. The stoma extender of claim 1, wherein the first end comprises a seal for sealing against the intestinal wall.

6. The stoma extender of claim 5, wherein the seal is selected from: an inflatable seal, a seal comprising resilient fingers, and a seal comprising a material that expands when contacted by moisture from stomal effluent.

7. The stoma extender of claim 1, wherein the second end comprises a member or portion that is stiffer than a portion of the conduit portion extending to the second end.

8. The stoma extender of claim 7, wherein the second end comprises a source of inflation fluid for the first end.

9. The stoma extender of claim 1, wherein at least a portion of the conduit portion is elastic.

10. The stoma extender of claim 1, further comprising an adhesive for retaining the second end, whereby an adjusted length of the conduit portion is stably held.

11. A stoma extender comprising:
    a first end for insertion into a stoma for diverting stomal effluent into the stoma extender before the effluent exits the stoma;
    a second end for remaining external of the stoma, for providing a discharge exit for stomal effluent;
    a conduit portion coupled between the first and second ends, configured for communicating stomal effluent through the stoma extender, wherein the conduit portion has a tapered shape from the second end to the first end so as to function as an adjustment to various fascia to skin distances, and wherein the conduit portion is elastic;
    an inflatable seal at the first end for sealing against the intestinal wall behind the stoma when the inflatable seal is inflated, while allowing for the diversion of stomal effluent into the stoma extender;
    an inflation fluid reservoir integrated with provided at the second end, or nearer the second end than the first end, for storing inflation fluid prior to delivery to the inflatable seal, the inflation fluid reservoir having a storage capacity sufficient to inflate the inflatable seal to an operative inflated state in use; and
    an inflation conduit for delivering inflation fluid from the inflation fluid reservoir to the inflatable seal;
    wherein the inflatable seal is toroidal in shape and sealed to or continuous with the tapered conduit portion at the first end; and wherein the inflation conduit is adapted to extend substantially within the stoma.

12. The stoma extender of claim 11, wherein the inflation fluid reservoir comprises an elastic container for storing the inflation fluid under pressure greater than atmospheric pressure.

13. The stoma extender of claim 11, wherein the inflation fluid reservoir is provided at the second end, or nearer the second end that the first end.

14. The stoma extender of claim 13, wherein the inflation fluid reservoir has a toroidal shape.

15. The stoma extender of claim 13, wherein the inflation reservoir is responsive to manual pressure applied at the second end, while rolling, folding, or pressing the second end towards stoma level during fitting of the stoma extender, to urge inflation fluid out of the reservoir.

16. The stoma extender of claim 11, wherein the first end has a collapsed configuration.

17. The stoma extender of claim 16, wherein the collapsed configuration is retained by a water soluble or water-dispersible glue or coating at the first end.

18. The stoma extender of claim 17, wherein the glue or coating comprises gelatin.

19. The stoma extender of claim 11 wherein at least the inflation fluid reservoir is initially contained within removable packaging, the removable packaging containing a second reservoir of the inflation fluid at a pressure not substantially less than the pressure within the inflation fluid reservoir.

20. The stoma extender of claim 19, wherein the removable packaging is made of barrier material for blocking transpiration of inflation fluid through the removable packaging.

21. A stoma extender comprising:
   a first end for insertion into a stoma for diverting stomal effluent into the stoma extender before the effluent exits the stoma;
   a second end for remaining external of the stoma, for providing a discharge exit for stomal effluent;
   a conduit portion coupled between the first and second ends, configured for communicating stomal effluent through the stoma extender, wherein the conduit portion has a tapered shape from the second end to the first end so as to function as an adjustment to various fascia to skin distances, and wherein the conduit portion is elastic;
   an inflatable seal at the first end for sealing against the intestinal wall behind the stoma when the inflatable seal is inflated, while allowing for the diversion of stomal effluent into the stoma extender;
   an inflation fluid reservoir for storing inflation fluid prior to delivery to the inflatable seal, the inflation fluid reservoir having a storage capacity sufficient to inflate the inflatable seal to an operative inflated state in use, wherein the inflation fluid reservoir is provided at the second end, or nearer the second end than the first end, and wherein the inflation reservoir is responsive to manual pressure applied at the second end, while rolling, folding, or pressing the second end towards stoma level during fitting of the stoma extender, to urge inflation fluid out of the reservoir; and
   an inflation conduit for delivering inflation fluid from the inflation fluid reservoir to the inflatable seal;
   wherein the inflatable seal is toroidal in shape and sealed to or continuous with the tapered conduit portion at the first end; and wherein the inflation conduit is adapted to extend substantially within the stoma.

* * * * *

UNITED STATES PATENT AND TRADEMARK OFFICE
CERTIFICATE OF CORRECTION

PATENT NO. : 10,045,877 B2
APPLICATION NO. : 12/999646
DATED : August 14, 2018
INVENTOR(S) : Bret Weig It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 80 days.

Signed and Sealed this
Twenty-seventh Day of August, 2019

Andrei Iancu
*Director of the United States Patent and Trademark Office*